United States Patent
Dale et al.

(10) Patent No.: US 8,863,772 B2
(45) Date of Patent: Oct. 21, 2014

(54) OCCLUDER FOR A MEDICAL INFUSION SYSTEM

(75) Inventors: James D. Dale, Nashua, NH (US); Jesse T. Bodwell, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 499 days.

(21) Appl. No.: 12/198,947

(22) Filed: Aug. 27, 2008

(65) Prior Publication Data

US 2010/0057016 A1 Mar. 4, 2010

(51) Int. Cl.
*F16K 31/06* (2006.01)
*F16K 7/04* (2006.01)
*A61M 5/00* (2006.01)
*A61M 39/28* (2006.01)
*A61M 5/168* (2006.01)
*F16K 31/14* (2006.01)
*F16K 7/06* (2006.01)
*A61M 1/34* (2006.01)
*A61M 1/16* (2006.01)

(52) U.S. Cl.
CPC .............. *F16K 31/14* (2013.01); *A61M 39/281* (2013.01); *A61M 1/3496* (2013.01); *A61M 5/16881* (2013.01); *A61M 39/28* (2013.01); *F16K 7/06* (2013.01); *A61M 1/16* (2013.01)
USPC ................... 137/595; 251/5; 251/7; 604/248; 604/250

(58) Field of Classification Search
USPC ....... 604/246–250; 417/392; 137/595; 251/4, 251/5, 7, 14
See application file for complete search history.

(56) References Cited

U.S. PATENT DOCUMENTS

| 350,850 A | 10/1886 | Tatum |
| 2,816,514 A | 12/1957 | Freese |

(Continued)

FOREIGN PATENT DOCUMENTS

| EP | 0 815 882 A2 | 1/1998 |
| EP | 0 815 882 A2 | 3/1998 |

(Continued)

OTHER PUBLICATIONS

International Search Report and Written Opinion for International Application No. PCT/US2008/011663, mailed Feb. 20, 2009.

(Continued)

*Primary Examiner* — Kevin C Sirmons
*Assistant Examiner* — William Carpenter
(74) *Attorney, Agent, or Firm* — Wolf, Greenfield & Sacks, P.C.

(57) ABSTRACT

The present invention generally relates to occluders and, in particular, to occluders for use in medical infusion systems. In one aspect, the occluder contains one or more tubes through which fluid can flow, and the occluder can be automatically controlled to allow or at least partially prevent fluid flow. In some cases, the occluder may be constructed and arranged to fail (e.g., due to loss of power) in a "closed" position, i.e., a position that at least partially prevents fluid flow. In addition, in one embodiment, the occluder may be manually overridden, even when in a failed state, by a user. For instance, in the event of a power failure, a user may be able to manually override the occluder to remove tubing from the occluder. Such occluders may find use, for example, in medical devices such as hemodialysis machines, medical infusion pumps, plasmapheresis devices, and the like.

25 Claims, 7 Drawing Sheets

(56) References Cited

U.S. PATENT DOCUMENTS

| | | | |
|---|---|---|---|
| 2,985,192 A * | 5/1961 | Taylor et al. | 137/627.5 |
| 3,111,125 A | 11/1963 | Schulte et al. | |
| 3,335,753 A * | 8/1967 | Kiser | 137/624.11 |
| 3,411,534 A * | 11/1968 | Rose | 137/595 |
| 3,539,081 A | 11/1970 | Norton et al. | |
| 3,568,214 A | 3/1971 | Goldschmied et al. | |
| 3,575,161 A * | 4/1971 | London | 604/31 |
| 3,759,483 A | 9/1973 | Baxter | |
| 3,827,561 A | 8/1974 | Serfass et al. | |
| 3,918,490 A * | 11/1975 | Goda | 137/597 |
| 3,991,972 A * | 11/1976 | Eaton | 251/11 |
| 4,061,142 A * | 12/1977 | Tuttle | 604/34 |
| 4,096,211 A | 6/1978 | Rameau | |
| 4,161,264 A | 7/1979 | Malmgren et al. | |
| 4,259,985 A * | 4/1981 | Bergmann | 137/595 |
| 4,322,054 A | 3/1982 | Campbell | |
| 4,398,908 A | 8/1983 | Siposs | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,484,599 A * | 11/1984 | Hanover et al. | 137/636.1 |
| 4,501,405 A | 2/1985 | Usry | |
| 4,575,007 A * | 3/1986 | Groth et al. | 239/310 |
| 4,585,442 A | 4/1986 | Mannes | |
| 4,594,058 A | 6/1986 | Fischell | |
| 4,623,450 A | 11/1986 | Vantard et al. | |
| 4,645,489 A * | 2/1987 | Krumme et al. | 604/245 |
| 4,725,269 A * | 2/1988 | Danby et al. | 604/250 |
| 4,778,451 A | 10/1988 | Kamen | |
| 4,808,161 A | 2/1989 | Kamen | |
| 4,826,482 A | 5/1989 | Kamen | |
| 4,828,543 A | 5/1989 | Weiss et al. | |
| 4,833,329 A * | 5/1989 | Quint et al. | 250/432 PD |
| 4,878,646 A * | 11/1989 | Edelman et al. | 251/9 |
| 4,969,486 A * | 11/1990 | Puzio | 137/624.18 |
| 4,976,162 A | 12/1990 | Kamen | |
| 5,002,471 A | 3/1991 | Perlov | |
| 5,088,515 A | 2/1992 | Kamen | |
| 5,105,981 A | 4/1992 | Gehman | |
| 5,113,906 A * | 5/1992 | Hogner | 137/595 |
| 5,178,182 A | 1/1993 | Kamen | |
| 5,300,044 A | 4/1994 | Classey et al. | |
| 5,318,414 A | 6/1994 | Lundback | |
| D350,823 S | 9/1994 | Lanigan | |
| D350,850 S | 9/1994 | Angelini | |
| 5,350,357 A | 9/1994 | Kamen et al. | |
| 5,351,686 A | 10/1994 | Steuer et al. | |
| 5,411,472 A | 5/1995 | Steg, Jr. et al. | |
| 5,413,566 A * | 5/1995 | Sevrain et al. | 604/248 |
| 5,421,823 A | 6/1995 | Kamen et al. | |
| 5,423,738 A | 6/1995 | Robinson et al. | |
| 5,429,485 A | 7/1995 | Dodge | |
| 5,431,626 A | 7/1995 | Bryant et al. | |
| 5,438,510 A | 8/1995 | Bryant et al. | |
| 5,441,231 A | 8/1995 | Payne et al. | |
| 5,441,636 A | 8/1995 | Chevallet et al. | |
| 5,472,325 A | 12/1995 | Svendsen | |
| 5,474,683 A | 12/1995 | Bryant et al. | |
| 5,575,310 A | 11/1996 | Kamen et al. | |
| 5,578,012 A | 11/1996 | Kamen et al. | |
| 5,628,908 A | 5/1997 | Kamen et al. | |
| 5,634,896 A | 6/1997 | Bryant et al. | |
| 5,690,831 A | 11/1997 | Kenley et al. | |
| 5,692,729 A | 12/1997 | Harhen | |
| 5,901,745 A * | 5/1999 | Buchtel | 137/595 |
| 5,931,648 A | 8/1999 | Del Canizo | |
| 5,938,634 A | 8/1999 | Packard | |
| 5,947,931 A | 9/1999 | Bierman | |
| 5,989,423 A | 11/1999 | Kamen et al. | |
| 6,041,801 A | 3/2000 | Gray et al. | |
| 6,105,416 A * | 8/2000 | Nelson et al. | 73/23.2 |
| 6,223,130 B1 | 4/2001 | Gray et al. | |
| 6,270,673 B1 | 8/2001 | Belt et al. | |
| 6,302,653 B1 | 10/2001 | Bryant et al. | |
| 6,382,923 B1 | 5/2002 | Gray | |
| 6,416,293 B1 | 7/2002 | Bouchard et al. | |
| 6,485,263 B1 | 11/2002 | Bryant et al. | |
| 6,497,676 B1 | 12/2002 | Childers et al. | |
| 6,595,948 B2 | 7/2003 | Suzuki et al. | |
| 6,604,908 B1 | 8/2003 | Bryant et al. | |
| 6,663,359 B2 | 12/2003 | Gray | |
| 6,722,865 B2 * | 4/2004 | Domroese | 417/477.11 |
| 6,749,403 B2 | 6/2004 | Spencer et al. | |
| 6,808,369 B2 | 10/2004 | Gray et al. | |
| 6,877,713 B1 | 4/2005 | Gray et al. | |
| 6,905,479 B1 | 6/2005 | Bouchard et al. | |
| 6,949,079 B1 | 9/2005 | Westberg et al. | |
| 7,124,996 B2 | 10/2006 | Clarke et al. | |
| 7,461,968 B2 | 12/2008 | Demers et al. | |
| 7,469,874 B2 * | 12/2008 | Akahori | 251/7 |
| 7,559,524 B2 | 7/2009 | Gray et al. | |
| 7,766,301 B2 | 8/2010 | Gray et al. | |
| 7,794,141 B2 | 9/2010 | Perry et al. | |
| 7,967,022 B2 | 6/2011 | Grant et al. | |
| 8,042,563 B2 | 10/2011 | Grant et al. | |
| 8,246,826 B2 | 8/2012 | Wilt et al. | |
| 8,273,049 B2 | 9/2012 | Demers et al. | |
| 8,292,594 B2 | 10/2012 | Tracey et al. | |
| 8,317,492 B2 | 11/2012 | Demers et al. | |
| 8,357,298 B2 | 1/2013 | Demers et al. | |
| 8,393,690 B2 | 3/2013 | Grant et al. | |
| 8,409,441 B2 | 4/2013 | Wilt | |
| 8,425,471 B2 | 4/2013 | Grant et al. | |
| 8,459,292 B2 | 6/2013 | Wilt et al. | |
| 8,491,184 B2 | 7/2013 | Kamen et al. | |
| 8,499,780 B2 | 8/2013 | Wilt et al. | |
| 8,545,698 B2 | 10/2013 | Wilt et al. | |
| 8,562,834 B2 | 10/2013 | Kamen et al. | |
| 2003/0194328 A1 | 10/2003 | Bryant et al. | |
| 2003/0220605 A1 | 11/2003 | Bowman, Jr. et al. | |
| 2004/0091374 A1 | 5/2004 | Gray | |
| 2004/0136843 A1 | 7/2004 | Jahn et al. | |
| 2005/0069425 A1 * | 3/2005 | Gray et al. | 417/392 |
| 2005/0095152 A1 * | 5/2005 | Dale | 417/477.2 |
| 2005/0095154 A1 | 5/2005 | Tracey et al. | |
| 2008/0015493 A1 | 1/2008 | Childers et al. | |
| 2008/0058697 A1 | 3/2008 | Kamen et al. | |
| 2008/0175719 A1 | 7/2008 | Tracey et al. | |
| 2008/0208103 A1 | 8/2008 | Demers et al. | |
| 2008/0216898 A1 | 9/2008 | Grant et al. | |
| 2008/0253427 A1 | 10/2008 | Kamen et al. | |
| 2008/0253911 A1 | 10/2008 | Demers et al. | |
| 2008/0253912 A1 | 10/2008 | Demers et al. | |
| 2008/0287854 A1 | 11/2008 | Sun | |
| 2009/0004033 A1 | 1/2009 | Demers et al. | |
| 2009/0008331 A1 | 1/2009 | Wilt et al. | |
| 2009/0012448 A1 | 1/2009 | Childers et al. | |
| 2009/0012449 A1 | 1/2009 | Lee et al. | |
| 2009/0012453 A1 | 1/2009 | Childers et al. | |
| 2009/0012454 A1 | 1/2009 | Childers | |
| 2009/0012455 A1 | 1/2009 | Childers et al. | |
| 2009/0012456 A1 | 1/2009 | Childers et al. | |
| 2009/0012457 A1 | 1/2009 | Childers et al. | |
| 2009/0012458 A1 | 1/2009 | Childers et al. | |
| 2009/0012461 A1 | 1/2009 | Childers et al. | |
| 2009/0095679 A1 | 4/2009 | Demers et al. | |
| 2009/0101549 A1 | 4/2009 | Kamen et al. | |
| 2009/0105629 A1 | 4/2009 | Grant et al. | |
| 2009/0107335 A1 | 4/2009 | Wilt et al. | |
| 2009/0107902 A1 | 4/2009 | Childers et al. | |
| 2009/0112151 A1 | 4/2009 | Childers et al. | |
| 2009/0114582 A1 | 5/2009 | Grant et al. | |
| 2009/0202367 A1 | 8/2009 | Gray et al. | |
| 2010/0051529 A1 | 3/2010 | Grant et al. | |
| 2010/0051551 A1 | 3/2010 | Grant et al. | |
| 2010/0056975 A1 | 3/2010 | Dale et al. | |
| 2010/0192686 A1 | 8/2010 | Kamen et al. | |
| 2010/0296953 A1 | 11/2010 | Gray et al. | |
| 2011/0098635 A1 | 4/2011 | Helmore et al. | |
| 2011/0105877 A1 | 5/2011 | Wilt et al. | |
| 2011/0218600 A1 | 9/2011 | Kamen et al. | |
| 2011/0299358 A1 | 12/2011 | Wilt et al. | |
| 2012/0106289 A1 | 5/2012 | Wilt et al. | |
| 2012/0207627 A1 | 8/2012 | Demers et al. | |

(56) References Cited

U.S. PATENT DOCUMENTS

| | | |
|---|---|---|
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0126413 A1 | 5/2013 | Van der Merwe et al. |
| 2013/0177457 A1 | 7/2013 | Demers et al. |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |

FOREIGN PATENT DOCUMENTS

| | | |
|---|---|---|
| JP | 2003-000704 A | 1/2003 |
| WO | WO 99/10028 A1 | 3/1999 |
| WO | WO 2006/120415 A1 | 11/2006 |
| WO | WO 2008/106191 A2 | 9/2008 |
| WO | WO 2009/051669 A1 | 4/2009 |
| WO | WO 2009/094179 A2 | 7/2009 |

OTHER PUBLICATIONS

International Preliminary Report on Patentability for International Application No. PCT/US2008/011663, issued Apr. 13, 2010.
International Search Report and Written Opinion for International Application No. PCT/US2009/000433, mailed Sep. 25, 2009.
International Preliminary Report on Patentability for International Application No. PCT/US2009/000433, mailed Aug. 5, 2010.
Invitation to Pay Additional Fees for International Application No. PCT/US2009/000433, mailed Jun. 4, 2009.
Partial European Search Report for Application No. EP 11150584.8, mailed Mar. 30, 2011.
Examination Report for EP Application No. 09703486.2 filed Jan. 23, 2009, published as EP 2254615 on Dec. 1, 2010, which Examination Report is dated May 4, 2012, and claims as pending for EP Application No. 09703486.2 as of May 4, 2012.
Response to Communication dated May 4, 2012 for EP Application No. 09703486.2 filed Jan. 23, 2009, which Response is dated Nov. 14, 2012, and claims as pending for EP Application No. 09703486.2 as of Nov. 14, 2012.
Office Action for MX Application No. MX/A/2010/008011 filed Jan. 23, 2009, which Office Action is dated Aug. 27, 2013, and claims as pending for MX Application No. MX/A/2010/008011 as of Aug. 27, 2013.
Invitation to Pay Additional Fees for Application No. PCT/US2009/000433 mailed Jun. 4, 2009.
International Search Report and Written Opinion for Application No. PCT/US2009/000433 mailed Sep. 25, 2009.
International Preliminary Report on Patentability for Application No. PCT/US2009/000433 mailed Aug. 5, 2010.
Office Action for U.S. Appl. No. 09/357,645, filed Jul. 20, 1999, which Office Action is dated Jun. 23, 2000, and claims as pending for U.S. Appl. No. 09/357,645 as of Jun. 23, 2000.
Office Action for U.S. Appl. No. 09/357,645, filed Jul. 20, 1999, which Office Action is dated Jan. 16, 2001, and claims as pending for U.S. Appl. No. 09/357,645 as of Jan. 16, 2001.
Office Action for U.S. Appl. No. 09/357,645, filed Jul. 20, 1999, which Office Action is dated May 17, 2002, and claims as pending for U.S. Appl. No. 09/357,645 as of May 17, 2002.
Examiner's Answer to Appeal Brief for U.S. Appl. No. 09/357,645, filed Jul. 20, 1999, which Answer is dated Feb. 25, 2003, and claims as pending for U.S. Appl. No. 09/357,645 as of Feb. 25, 2003.
BPAI Decision on Appeal for U.S. Appl. No. 09/357,645, filed Jul. 20, 1999, which Decision is dated Jan. 30, 2004, and claims as pending for U.S. Appl. No. 09/357,645 as of Jan. 30, 2004.
Office Action for U.S. Appl. No. 10/951,441, filed Sep. 28, 2004, published as US 2005-0069425 on Mar. 31, 2005 which Office Action is dated Sep. 1, 2005, and claims as pending for U.S. Appl. No. 10/951,441 as of Sep. 1, 2005.
Office Action for U.S. Appl. No. 10/951,441, filed Sep. 28, 2004, published as US 2005-0069425 on Mar. 31, 2005 which Office Action is dated May 5, 2006, and claims as pending for U.S. Appl. No. 10/951,441 as of May 5, 2006.
Office Action for U.S. Appl. No. 10/951,441, filed Sep. 28, 2004, published as US 2005-0069425 on Mar. 31, 2005 which Office Action is dated Dec. 4, 2007 and claims as pending for U.S. Appl. No. 10/951,441 as of Dec. 4, 2007.
Office Action for U.S. Appl. No. 10/951,441, filed Sep. 28, 2004, published as US 2005-0069425 on Mar. 31, 2005 which Office Action is dated Aug. 20, 2008, and claims as pending for U.S. Appl. No. 10/951,441 as of Aug. 20, 2008.
Office Action for U.S. Appl. No. 12/423,665, filed Apr. 14, 2009, published as US 2009-0202367 on Aug. 13, 2009 which Office Action is dated Jun. 26, 2009, and claims as pending for U.S. Appl. No. 12/423,665 as of Jun. 26, 2009.
Office Action for U.S. Appl. No. 12/864,293, filed Dec. 9, 2010, published as US 2011-0098635 on Apr. 28, 2011, which Office Action is dated Aug. 20, 2013, and claims as pending for U.S. Appl. No. 12/864,293 as of Aug. 20, 2013.

* cited by examiner

OCCLUDER FOR A MEDICAL INFUSION SYSTEM

FIELD OF INVENTION

The present invention generally relates to occluders and, in particular, to occluders for use in medical infusion systems.

BACKGROUND

Medical devices such as hemodialysis machines, medical infusion pumps, plasmapheresis devices, and the like often require the use of tubing to move fluids, e.g., to or from a subject for infusion. Such tubing can be made out of materials such as nylon, rubber, polyvinyl chloride, polyurethane, or polyethylene. However, control of the flow of fluids in the tubing is important in many applications.

SUMMARY OF THE INVENTION

The present invention generally relates to occluders and, in particular, to occluders for use in medical infusion systems. The subject matter of the present invention involves, in some cases, interrelated products, alternative solutions to a particular problem, and/or a plurality of different uses of one or more systems and/or articles.

One aspect of the invention is directed to an occluder for occluding at least one collapsible tube of a medical infusion device. In one set of embodiments, the occluder comprises a base defining a pathway for the collapsible tube, an occluding member rotationally movable about a pivot immobilized relative to the base, and a biasing member exerting a biasing force on the occluding member. In one embodiment, the occluding member comprises an occluding element portion that at least partially obstructs the pathway when the occluding member is in a first position but that does not obstruct the pathway when the occluding member is in a second position. In certain cases, the biasing force urges the occluding member to move into or remain in the first position.

The occluder, in another set of embodiments, includes a base defining a pathway for the collapsible tube, an occluding member comprising an occluding element portion that at least partially obstructs the pathway when the occluding member is in a first position but that does not obstruct the pathway when the occluding member is in a second position, a biasing member exerting a biasing force on the occluding member, and a grip member forming part of or immobilized with respect to the occluding member, the grip member being movable between a first position and a second position. In one embodiment, the biasing force urges the occluding member to move into or remain in the first position. In addition, movement of the grip member from the first position into the second position, in certain instances, moves the occluding member from the first position into the second position.

The occluder, in yet another set of embodiments, includes a base defining a pathway for the collapsible tube, an occluding member comprising an occluding element portion that at least partially obstructs the pathway when the occluding member is in a first position but that does not obstruct the pathway when the occluding member is in a second position, a pneumatic actuator having a fluidic inlet and a piston movable from a first position to a second position when the fluidic inlet is pressurized, and a grip member forming part of or immobilized with respect to the occluding member, the grip member being movable between a first position and a second position. The movable piston, in one embodiment, is mechanically interconnected with the occluding member such that extension of the movable piston into the second position causes the occluding member to move into the second position. In some cases, movement of the grip member from the first position into the second position moves the occluding member from the first position into the second position.

In still another set of embodiments, the occluder includes a base defining a pathway for the collapsible tube, an occluding member rotationally movable about a pivot immobilized relative to the base, a lever arm having a first end connected to the pivot, an actuator comprising a movable piston immobilized relative to the base, a biasing spring biased to move the lever arm into the first position, and a grip member forming part of or immobilized with respect to the occluding member. In one embodiment, the occluding member comprises an occluding element portion that at least partially obstructs the pathway when the occluding member is in a first position but that does not obstruct the pathway when the occluding member is in a second position. In some instances, the lever arm is rotationally movable about the pivot between a first position to a second position, and in certain cases, the lever arm moves the occluding member between the first position and the second position when the lever arm is moved from the first to the second position. In some instances, the piston is extendable upon actuation of the actuator from a first position to a second position, where extension of the piston into the second position causes the lever arm to move from the first position to the second position and the occluding member to move from the first position into the second position. In one embodiment, the grip member is movable between a first position and a second position, where movement of the grip member from the first position into the second position moves the occluding member from the first position into the second position.

In another aspect, the present invention is directed to a method of making one or more of the embodiments described herein, for example, an occluder. In another aspect, the present invention is directed to a method of using one or more of the embodiments described herein, for example, an occluder.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to occluders and, in particular, to occluders for use in medical infusion systems. In one aspect, the occluder contains one or more tubes through which fluid can flow, and the occluder can be automatically controlled to allow or at least partially prevent fluid flow. In some cases, the occluder may be constructed and arranged to fail (e.g., due to loss of power) in a "closed" position, i.e., a position that at least partially prevents fluid flow. In addition, in one embodiment, the occluder may be manually overridden, even when in a failed state, by a user. For instance, in the event of a power failure, a user may be able to manually override the occluder to remove tubing from the occluder. Such occluders may find use, for example, in medical devices such as hemodialysis machines, medical infusion pumps, plasmapheresis devices, and the like.

Figure 1A:
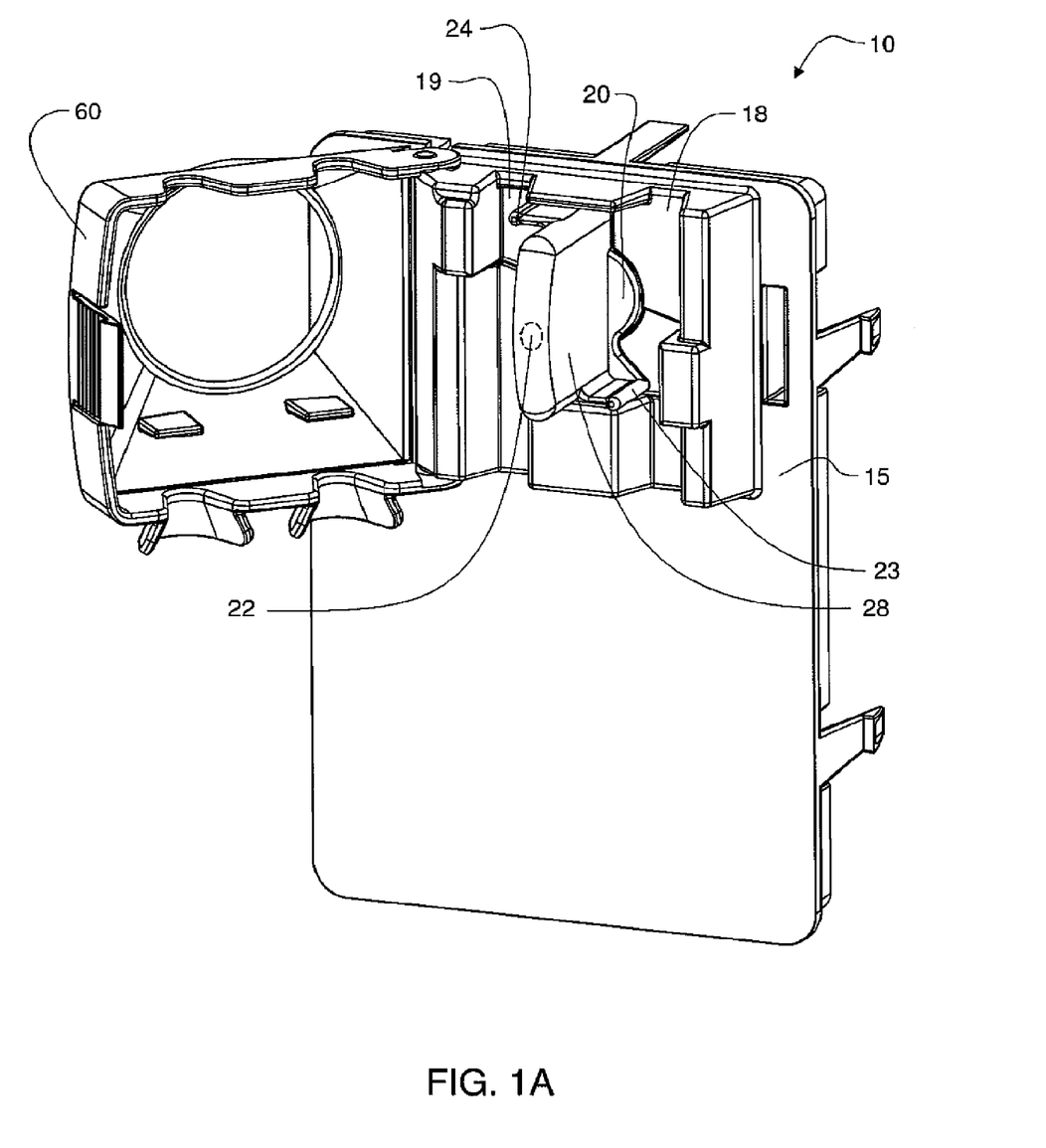
FIGS. 1A-1B illustrate an occluding member able to occlude a pathway, according to one embodiment of the invention.
Figure 1B:
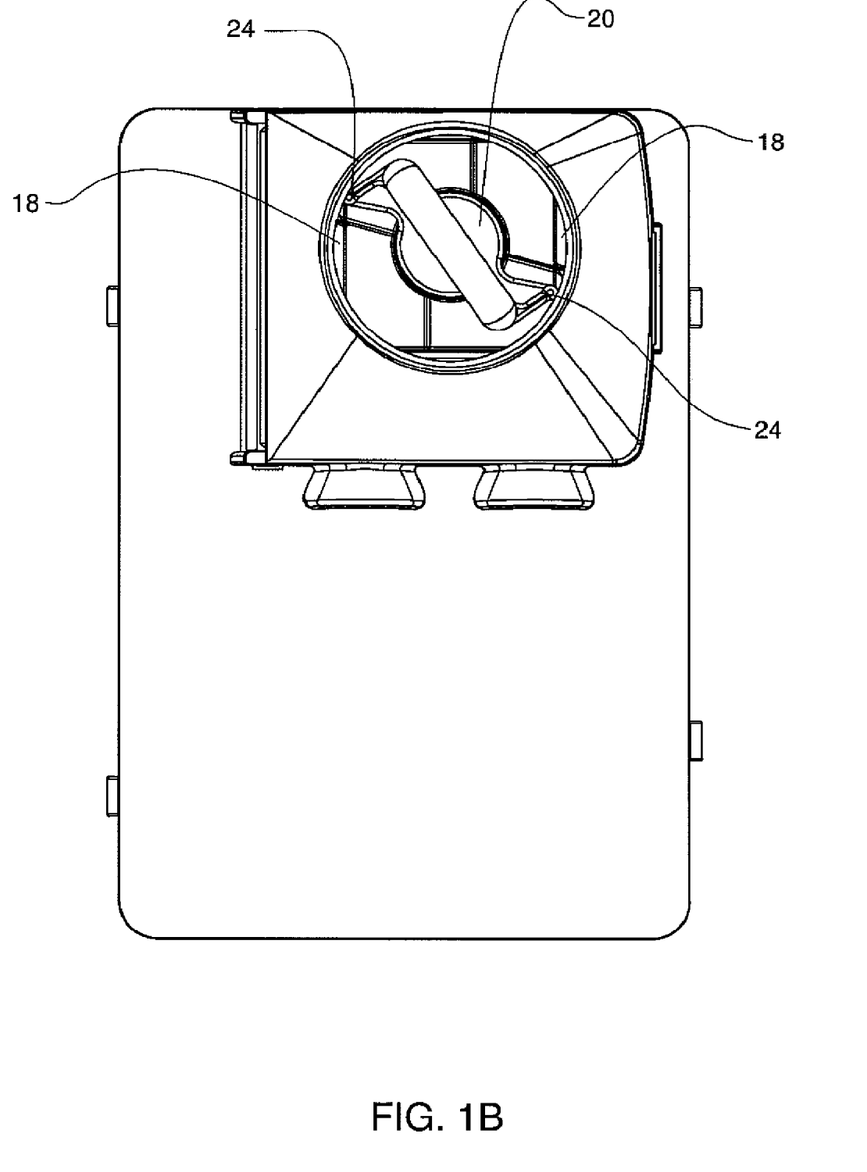

Referring now to FIG. 1, an example of one embodiment of the invention is shown. As discussed below, other configurations are also possible in other embodiments of the invention. FIG. 1A illustrates a front view of an occluder according to one embodiment of the invention, in which fluid flow through tubing can be controlled. For instance, when the occluder is in a first position, the tubing may be partially or completely constricted, thus reducing or preventing fluid flow; when the occluder is in a second position, however, the tubing may be open, allowing at least some fluid flow to occur.

In this figure, occluder 10 includes a base 15 and a pathway 18 for receiving tubing. As shown in this figure, pathway 18 is an indentation within base 15 shaped for receiving tubing. However, in other embodiments, pathway 18 may be defined on base 15 in other ways, for example, by one or more ridges on the surface of base 15, by fasteners, loops, or rings on the surface of base 15, or the like. In addition, although pathway 18 is shown as being substantially straight in this figure, in other embodiments, pathway 18 may be curved in some fashion. In some cases, the pathway may be designed to be slightly smaller than the tubing it is designed to carry, thus requiring some force and/or deformation of the tubing in order for it to be properly positioned within the pathway.

The tubing may be bendable or flexible, for example, so that the tubing can be at least partially collapsed when occluding element 24 pushes into the tubing. For example, the tube may be formed from materials such as silicone, nylon, rubber, polyvinyl chloride, polyurethane, polyethylene, or the like. In some cases, the tubing is biocompatible. The tubing may be used, for example, to transport blood or other substances to or from a subject, e.g., as part of a dialysis machine or other medical infusion system.

Positioned on base 15 is an occluding member 20 that is rotationally moveable about a pivot 22. The occluding member may rotate completely around the pivot, or in some cases, the occluding member can rotate only partially around pivot 22. Pivot 22 may be immobilized with respect to base 15. For instance, pivot 22 may be a screw or a rod, or a similar structure, that is affixed within base 15. Occluding member 20 may be constructed such that when it is rotated around pivot 22, occluding element 24 can enter and at least partially obstruct pathway 18. For instance, as is shown in FIG. 1B, when occluding member 20 is in a first position, occluding element 24 at least partially enters into pathway 18, at least partially obstructing pathway 18. Fluid flowing within tubing contained within pathway 18 may thus be partially or completely inhibited from flowing past occluding element 24. However, as is shown in FIG. 1A, when occluding member 20 is in a second position, occluding element 24 does not enter into pathway 18, and thus fluid contained within a tubing in pathway 18 is not obstructed by occluding element 24.

As shown here, occluding member 20 may be in one of two positions. In some cases, however, the occluding member may be positioned in more than two positions. For instance, occluding member 20 may contain more that one occluding element, which may each enter into or at least partially obstruct pathway 18 and/or other pathways present within base 15, or occluding member 20 may be constructed to be positioned in different positions, some of which may cause occluding element 24 to be present within pathway 18 to various degrees, thereby causing occlusion of fluid flow to varying degrees. Occluding element 24 may have any shape suitable to at least partially block or obstruct flow of fluid within tubing contained within pathway 18 when occluding element 24 enters into or at least partially obstructs the pathway. As depicted in FIG. 1A, occluding element 24 includes a semi-cylindrical shaped portion that enters pathway 18. However, other shapes may also be used, such as spheres, wedges, blocks, rods, or the like.

The occluding member may be controlled manually and/or automatically. For example, as illustrated in FIG. 1A, occluding member 20 may be manually controlled using grip member 28. Grip member 28 can be formed as part of, or otherwise immobilized with respect to occluding member 20. In this figure, grip member 28 is an external knob extending outward. However, in other embodiments, other forms of grips may be used, for example, handles, indentations, fingerholes, or the like. A user can grasp grip member 28 and rotate occluding member 20 manually, e.g., from a first position to a second position (or vice versa). By doing so, for instance, the user can move occluding element 24 into and/or out of pathway 18, e.g., as is illustrated in FIGS. 1A and 1B. In some cases, the force required to rotate occluding member 20 using grip member 28 may be reasonably low, i.e., such that a user can readily rotate occluding member 20 about pivot 22, for example, with the thumb and forefinger without excess exertion. In other cases, however, more force may be needed.

As is shown in FIG. 1A, grip member 28 is shown to be a part of occluding member 20. However, in other embodiments, grip member 28 may be separate from occluding member 20. For example, grip member 28 may be a separate knob, crank, handle, lever, etc. that is turned or otherwise moved in order to turn occluding member 20, and control of occluding member 20 by grip member 28 may be accomplished through the use of gears, belts, chains, or the like, mechanically coupling (directly or indirectly) movement of grip member 28 with occluding member 20.

In some cases, the occluding member may be automatically or externally controlled. For example, as is discussed below, the occluding member may be moved from a first position to a second position by using an actuator. Many different types of actuators may be used in various embodiments to control the occluding member, for example, electronically controlled actuators, fluidically controlled actuators, pneumatically controlled actuators, mechanically controlled actuators, magnetically controlled actuators, electromagnetically controlled actuators, or the like. An example of such an actuator is described now with reference to FIG. 2A. In this figure, showing a back view of an occluder (which is not necessarily the same one shown in FIG. 1A), base 15 includes pivot 22. Pivot 22 is the pivot around which an occluding member is able to at least partially rotate (not shown in FIG. 2A). It should be noted that although, in this example, the actuator is shown as being on the back of the occluder, the actuator may be positioned in any suitable location on the occluder, for example, on the front.

Figure 2A:
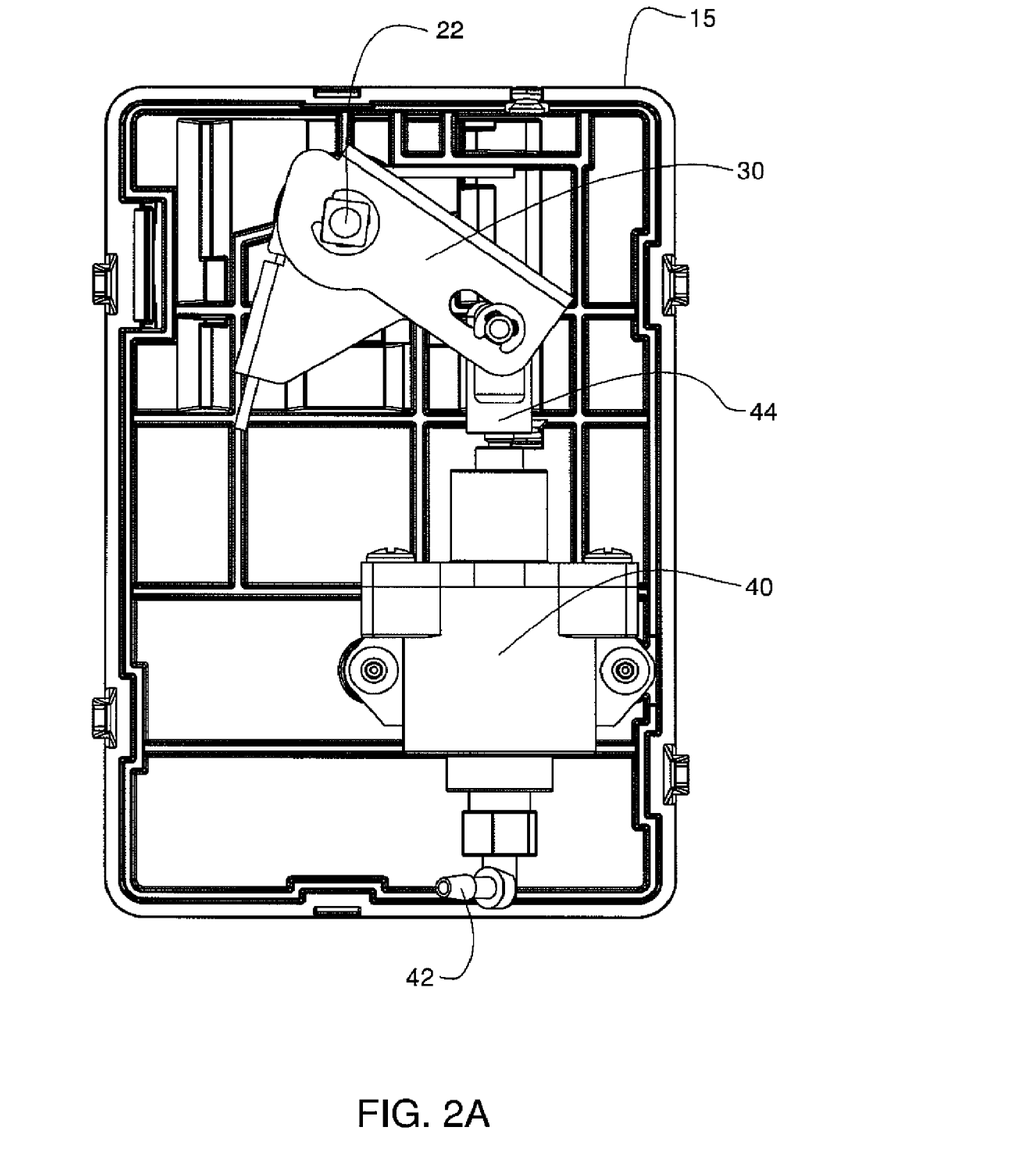
FIGS. 2A-2B illustrate an actuator for moving an occluding member, in another embodiment of the invention.

As is shown in FIG. 2A, an occluding member may be controlled through movement of a lever arm, such as lever arm 30. For instance, lever arm may be formed as part of or otherwise immobilized with respect to the occluding member, or movement of lever arm 30 may be otherwise mechanically coupled to movement of the occluding member, for example, using keys, gears, belts, chains, or the like. As a specific example, in one embodiment, the lever arm, the occluding member, and the pivot (and optionally the grip member) may all be all formed as a single entity. As another example, however, a key, a guide, a gear, a lever, or the like may be used to cause movement of the occluding member to occur when the lever arm is moved.

In one embodiment, as is shown in FIG. 2A, lever arm 30 is pivotably rotatable about pivot 22, such that movement of lever arm 30 around pivot 22 can cause movement of the occluding member to occur. The position of lever arm 30, in turn, may be controlled by actuator 40. Actuator 40 may be any suitable device with an output member 44 that can be controllably moved from (at least) a first position to a second position. For example, actuator 40 may include a motor, a hydraulically or pneumatically actuated piston acting within a cylinder on an output shaft, or the like. The position of actuator 40 may be controlled using any suitable technique. For instance, movement of actuator 40 from a first position to a second position may be accomplished using electronic controls, pneumatic controls, hydraulic controls, mechanical controls, electromagnetic controls, or the like. For example, in one embodiment, actuator 40 comprises a housing having a piston inside a stationary cylinder, and a movable element 44 (for example, an output shaft) that can be moved from a first position to a second position. In FIG. 2A, actuator 40 (e.g., having a pneumatically actuated piston) is shown with its output shaft 44 in a retracted position, and in FIG. 2B, the output shaft of actuator 40 is shown in an extended position. The output shaft of actuator 40 may be mechanically coupled to lever arm 30 using any suitable technique. For example, as is shown in FIG. 2A, lever arm 30 is mechanically coupled with respect to a movable element 44 of actuator 40, such that when the movable element 44 of actuator 40 moves from a first (retracted) position (FIG. 2A) to a second (extended) position (FIG. 2B), lever arm 30 also moves from a first position to a second position, which, in turn, can be used to move an occluding member, such as occluding member 20, as previously discussed.

As mentioned, the position of actuator 40 may be controlled, for instance, using electronic controls, fluidic controls, pneumatic controls, mechanical controls, electromagnetic controls, or the like. As a particular example, in some embodiments, the actuator may be pneumatically controlled. For example, control line 42 may be a fluidic control line in which fluid entering line 42 may cause actuator 40 to move from a first, compressed position to a second, extended position, thereby moving lever arm 30. The control fluid may be any suitable fluid, for example, air, oil or water. Thus, for example, air may be introduced to actuator 40 to cause the movement of the actuator (e.g., a piston) from a first position to a second position. In another embodiment, control line 42 transmits an electronic signal, for example, if actuator 40 is a motor or solenoid.

In some cases, the occluding member may be biased to remain in one position, for example, a first position. Thus, for instance, in the absence of any actuation (for example, if a control line such as control line 42 were somehow inoperative, e.g., due to a power outage, an unplugged cable, a leak, or the like), the occluding member would be biased such that it would remain in the first position, for example, partially or completely constricting tubing within the occluder. However, in some cases, the biasing may be such that it could be manually overridden (e.g., allowing movement of the occluding member to a second position), for instance by use of grip member 28, as previously discussed. Thus, for example, in the event of a power outage that causes the actuator to stop working, a biasing force may cause the occluding member to partially or completely constrict tubing within the occluder. The occluding member could then be moved manually (overcoming this biasing force), for instance, to remove the tubing in the event of an emergency. In this example, the occluder can be said to have failed in a "closed" position, meaning that in the absence of any power or control, the occluder reaches a state in which tubing is partially or completely constricted by the occluder.

Biasing of the occluding member may occur directly or indirectly, for instance, by applying a bias to a lever arm, an actuator, etc., that controls the position of the occluding member. An example of such a system is shown with reference to FIG. 3. In this figure, biasing of a lever arm 30 used to control movement of an occluding member is achieved by use of biasing member 50. Biasing member 50 may be any apparatus able to create a bias on the occluding member 20. For example, biasing member 50 may exert a biasing force on the occluding member 20, a lever arm 30 controlling the occluding member 20, an actuator 40 controlling the occluding member, or the like. Biasing member 50 may be, for instance, a spring, a weight, a pulley, a piston, a motor, or the like.

Figure 2B:
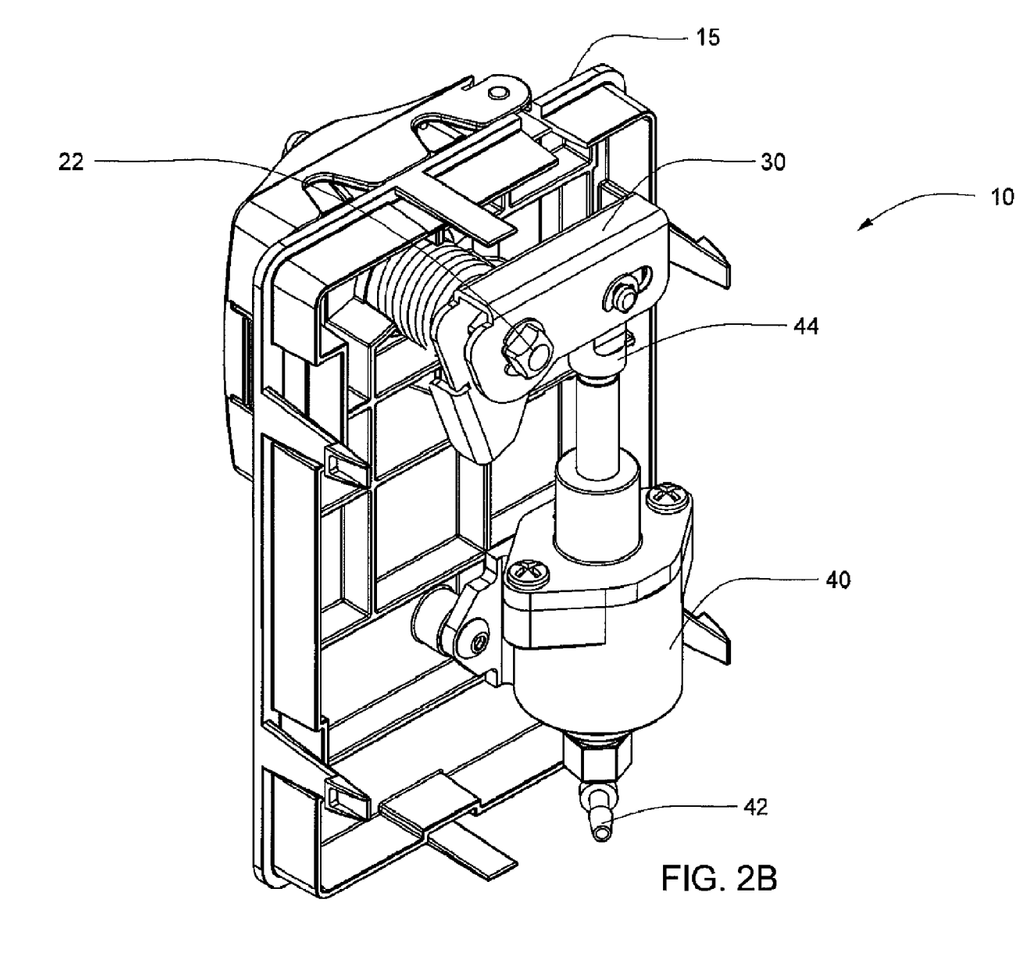
Figure 3:
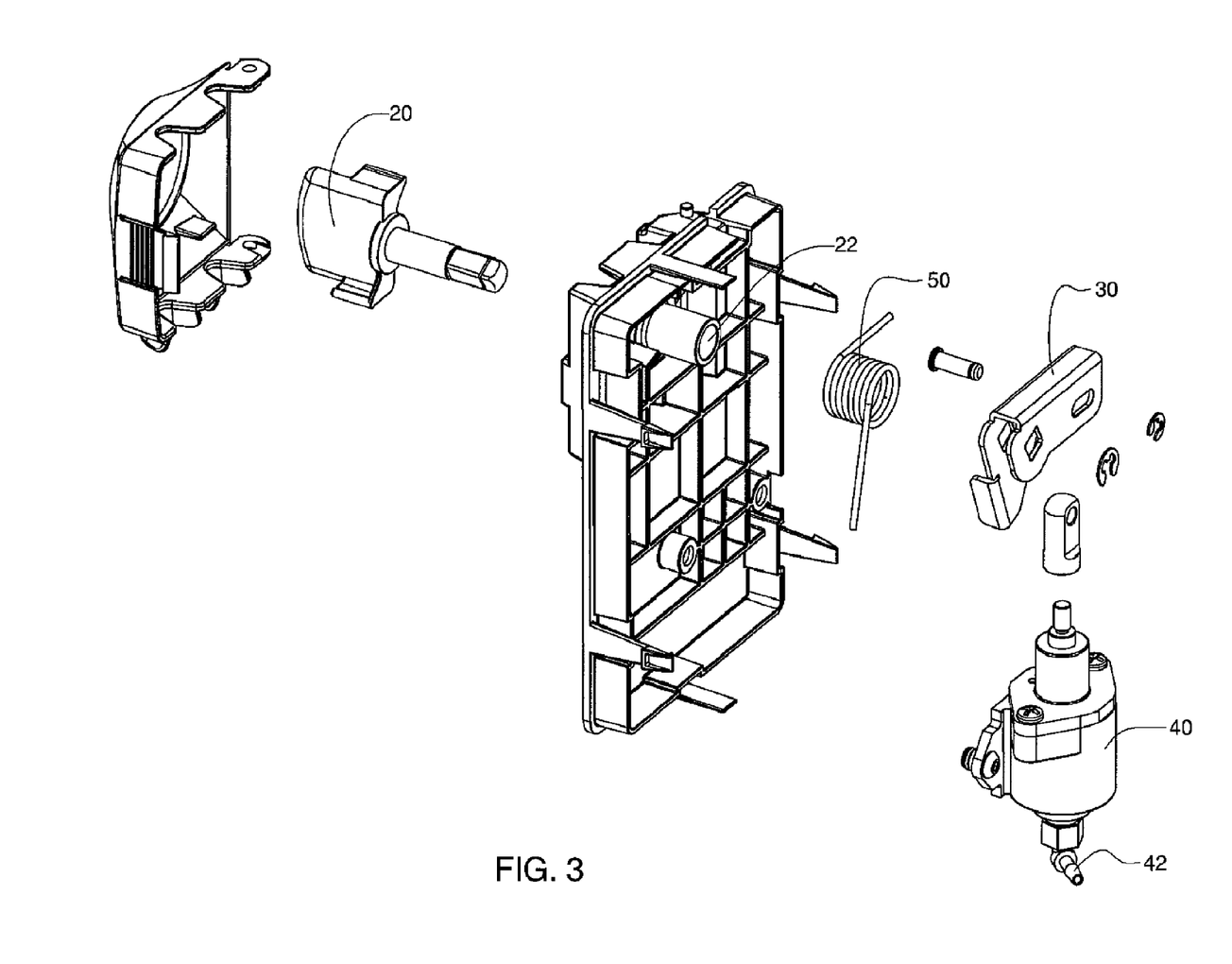
FIG. 3 is an exploded view of the back portion of an occluder showing a biasing member in yet another embodiment of the invention.

For instance, in FIG. 3, biasing member 50 is a torsion spring loaded to exert a rotational force around the axis of the pivot 22 of occluding member 20, and causing movement of lever arm 30 rotationally around pivot 22 down towards actuator 40. In the absence of any actuation from actuator 40, biasing member 50 is able to move lever arm 30 to a first position in which actuator 40 is in a first (retracted) position, similar to FIG. 2A, above. However, the biasing force created by spring 50 (or other biasing member) on lever arm 30 may be at least partially counteracted by a force from actuator 40, e.g., by using control line 42, such that the biasing force is overcome by the force from the actuator, and lever arm 30 moves into a second position, which in turn, moves the occluding member, e.g., as is shown in FIG. 2B.

More than one pathway for tubing may be present within the occluder, in one set of embodiments. In some cases the occluding member may control more than one occluding element 24, and/or there may be more than one occluding member present. For example, referencing FIG. 1A, base 15 in occluder 10 includes two pathways 18 and 19, and occluding member 20 includes two occluding elements 23 and 24 which can enter into and at least partially obstruct or occlude these pathways. In this example, occlusion of pathways 18 and 19 occurs synchronously, i.e., movement of occluding member 20 causes occlusion of both pathways to occur. However, in other embodiments, different degrees of occlusion of the first and second pathways can occur, and in some cases, one pathway may become occluded while another pathway is not occluded, or one pathway may become occluded while an occlusion is removed from another pathway.

In the event of a power failure, an alarm condition, or any other condition in which it is desirable to diminish or occlude fluid flow through the tubing placed in pathways 18 and 19, the actuating power to actuator 40 can be discontinued. For example, if actuator 40 is pneumatically powered, a power loss, alarm or failsafe condition can cause a relay valve in the pneumatic pathway to vent, thereby releasing pressure within the cylinder of actuator 40. Under the bias force of biasing member 50 (for example, a torsion spring), the lever arm 30 is moved to force the output shaft of actuator 40 into a retracted position, and the occluding member 20 into a first position, thereby causing the tubing to be at least partially occluded.

The release of power to actuator 40 may occur passively, for example, by a loss of power that also effects a loss of power to a ventable relay valve, for example. In other embodiments, an electronic control system through which an alarm or failsafe condition is declared can transmit a signal to an actively controlled relay that can halt power transmission to actuator 40. In a non-limiting example, a command to vent can be sent to a ventable relay situated in the pneumatic pathway of a pneumatically powered actuator 40, causing release of pneumatic pressure against the piston of actuator 40.

The occluder herein described provides for a number of advantages, including the ease with which it may be manually overridden. There may be circumstances in which it is desirable for an operator, clinician or patient to manually override the automatic actuation of occluder 20 to an occluding (first) position. For example, in a power loss or failsafe situation, it may be desirable to quickly return to a patient any blood remaining within a blood circuit of a hemodialysis system. If occluder 20 is included in the blood circuit of a hemodialysis system, the operator, clinician or patient needs to be able to release the occluder to allow for the return of the extracorporeal blood to the patient. The shape, size and function of occluder 20 provides a mechanical advantage for manual operation. The diameter of grip member 28 around its axis of rotation is sufficiently large to permit an individual to rotate it against the force of biasing member 50 with only the thumb and forefinger. For example, holding the occluder 20 in the open (second) position with one hand, the operator can use the other hand to lift the tubes from pathways 18 and 19 to completely disengage them from occluder 20. Conversely, relatively little effort is required to hold occluder 20 in the open (second) position in order to load new tubes into pathways 18 and 19.

Figure 4:
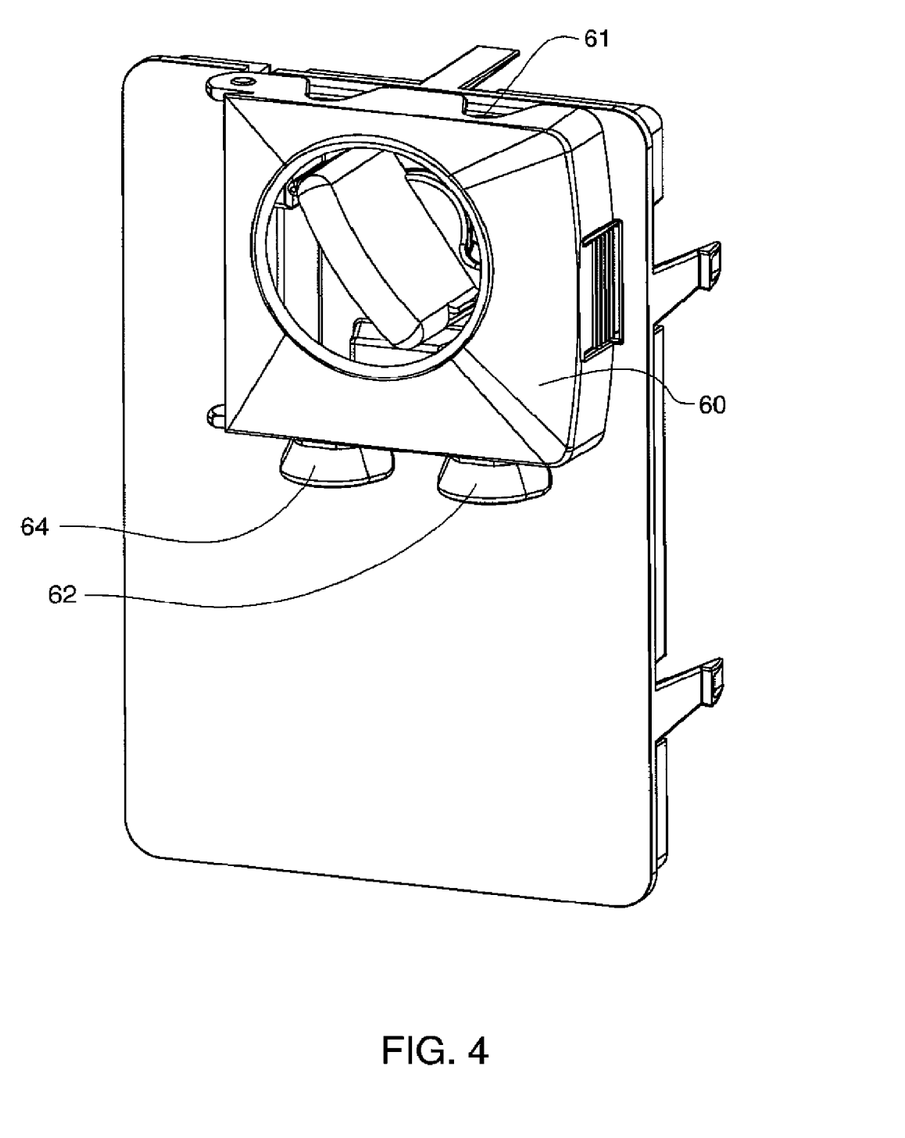
FIG. 4 illustrates an occluder with a cover, according to still another embodiment of the invention.

In one embodiment, a cover may be present on the occluder. The cover may be used, for example, to at least partially protect and/or conceal tubing and/or the occluding member (for example, if the cover is opaque or translucent). In some cases, the cover may be used to properly position tubing within the device. For example, referring now to FIG. 4, occluder assembly 10 includes base 15 and cover 60. In this example, cover 60 is shown hingeably attached to base 15, as shown in FIG. 1A. However, in other embodiments, cover 60 may be attached to the base using other techniques, for example, slideably attached, or cover 60 may be a separate unit that is mounted onto base unit 15. In FIG. 4, cover 60 includes an indentation 61 that can be used to properly position tubing within pathway 18 on base 15. The cover 60 may be shaped such that if tubing is not properly positioned within pathway 18, cover 60 cannot be properly closed onto base 15. Thus, a user will know that tubing is properly positioned within the occluder when the cover properly closes or otherwise mounts on the base. In one embodiment, the cover 60 can be constructed of transparent material such as a polycarbonate resin thermoplastic (LEXAN) (or other suitable plastic, polyethylene, polypropylene, or the like) to allow the user to visually confirm the proper positioning of the tubing in pathways 18 and/or 19, and the position of occluder 20.

In one set of embodiments, the base and/or the cover (if present) may include one or more flanges, which may prevent or at least reduce kinking or pinching of tubing within the occluder, e.g., on the edges of the base and/or the cover. For instance, in FIG. 4, base 15 and/or cover 60 includes flanged openings 62, 64. The flanges may have tilted or tapered portions that allow smooth bending of a tube around such portions. However, in other embodiments, other methods may be used to prevent or reduce kinking or pinching of tubing. For example, base 15 and/or cover 60 may have rounded or tapered shapes that prevent kinking of tubing coming into contact with the base or cover.

In another embodiment, a switch (not shown) may be mounted on base 15 or cover 60. The switch can be either in an "on" or "off" position upon opening of cover 60, and remain in the "on" or "off" position if cover 60 is not closed completely or properly. The indication by the switch of an open or incompletely closed cover 60 can be transmitted to an electronic control system, which in turn can trigger and transmit an alarm condition to the user, or otherwise prevent fluid flow through the tubes situated in pathways 18 and/or 19.

Figure 5:
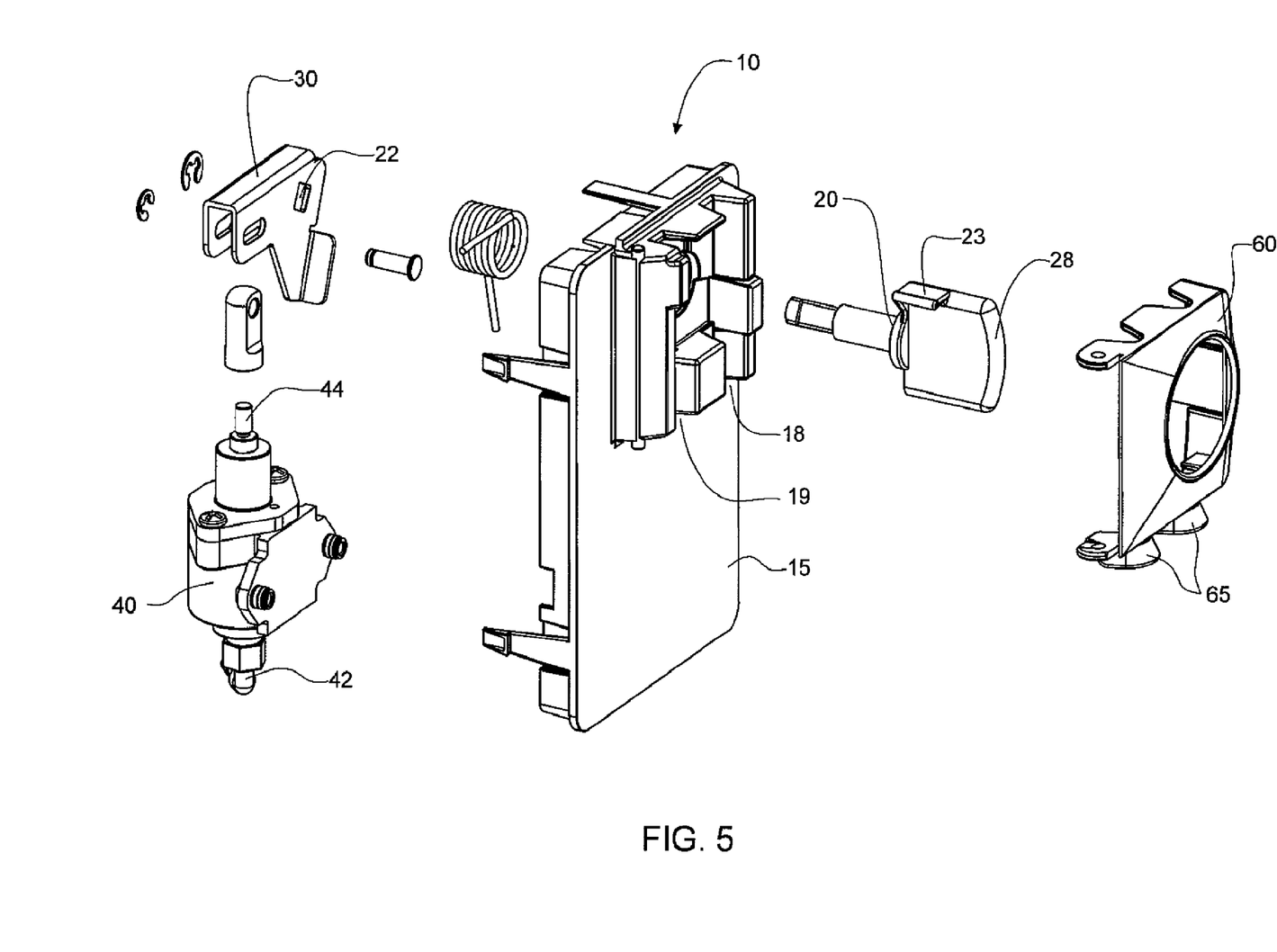
FIG. 5 is an exploded view of the front portion of an occluder according to another embodiment of the invention.

Another view of a non-limiting example of an occluder is shown in exploded form in FIG. 5. In this figure, occluder 10 includes base 15 and two pathways for tubing 18, 19. Occluding member 20 is rotatable about a pivot, which brings occluding elements 24 (not shown) and 23 into pathways 18 and 19, respectively. Occluding member 20 can be manually controlled using grip member 28, or automatically controlled using actuator 40. Actuator 40 includes a pneumatically controlled piston, with air entering through control line 42. When air enters actuator 40 through control line 42, the output shaft 44 extends, pushing lever arm 30. Movement of lever arm 30 around pivot 22 is mechanically coupled to movement of occluder member 20; thus, movement of the output shaft 44 of actuator 40 can be used to control occlusion by occlusion elements 24 and 23 into pathways 18 and 19. Also shown in FIG. 5 is cover 60 and flanges 65. Cover 60 is hingeably connected to base 15, and cannot be closed if tubing is present unless the tubing is properly positioned within pathways 18 or 19. Thus, when cover 60 is closed, the tubing has been properly positioned.

The occluder may be formed out of different materials, and different parts of an occluder device may not be all formed from the same material. For example, materials that can be used in the construction of the occluder include, but are not limited to, metals such as stainless steel, plastics such as polyethylene or polypropylene, or the like.

The occluder may be used in any suitable system in which occlusion of a fluid is desired. In one set of embodiments, the occluder may be used as part of a medical infusion device, for example, a dialysis or a hemodialysis system such as those disclosed in U.S. patent application Ser. No. 12/072,908, filed Feb. 27, 2008, published as US Patent Application Publication No. 2009/0008331-A1 on Jan. 8, 2009, and entitled "Hemodialysis Systems and Methods," by Wilt, et al., incorporated herein by reference.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An occluder for occluding at least two collapsible tubes of a medical infusion device, the occluder comprising:
    a base having a front surface defining two substantially parallel pathways along each of which a length of at least one of the collapsible tubes can be placed, and having an opposing back surface onto which an occluder actuator is mounted, wherein the base is configured for mounting onto the medical infusion device;
    an occluding member located on the front surface of the base between the pathways and comprising a pivot shaft having a long axis that extends through the base from the back surface to the front surface, and that is rotationally movable about a pivot axis coincident with the long axis of the pivot shaft, the pivot shaft being approximately perpendicular to said front and back surface of the base, the occluding member comprising a pair of tube-compressing elements on opposing sides of the pivot shaft, and that are rotationally movable upon rotation of the occluding member, such that when the at least two collapsible tubes are installed on the pathways of the front surface of the base, the tube-compressing elements at least partially obstruct both pathways to substantially restrict or essentially completely inhibit fluid flow through the collapsible tubes when the occluding member is rotated into an occluding position, but that do not obstruct the pathways to substantially restrict fluid flow through the collapsible tubes when the occluding member is rotated into a non-occluding position;
    the occluder actuator comprising an actuating shaft mechanically coupled to the pivot shaft, the actuating shaft having a long axis and a direction of travel that is approximately perpendicular to the pivot shaft and is arranged to cause rotation of the pivot shaft about the long axis of the pivot shaft, the occluder actuator further being a hydraulic or pneumatic actuator configured to move the actuating shaft when a fluid under pressure is delivered to the actuator;

wherein actuation of the actuator through introduction of the fluid causes movement of the actuating shaft and rotation of the occluding member in a direction that moves the tube-compressing elements away from the pathways.

2. The occluder of claim 1, wherein the actuator is pneumatic.

3. The occluder of claim 1, further comprising:
a biasing member on the base exerting a biasing force on the occluding member, the biasing force urging the occluding member to rotate the tube-compressing elements toward the respective pathways.

4. The occluder of claim 1, further comprising an openable cover mounted on the front surface of the base and adapted and configured to position and secure the tubes within the pathways when the cover is mounted onto the front surface of the base and in a closed position.

5. The occluder of claim 4, wherein the cover comprises a flanged opening allowing the tubes within the pathways to exit the cover when the cover is in a closed position.

6. The occluder of claim 1, wherein the medical infusion device is a dialysis device.

7. The occluder of claim 1, further comprising a grip member forming part of or immobilized with respect to the occluding member, the grip member being configured to permit a user to manually rotate the occluding member between the occluding position and the non-occluding position.

8. The occluder of claim 1, wherein the actuator comprises a piston in a cylinder, the piston being connected to the actuating shaft and moveable in the cylinder when the fluid under pressure is delivered to the cylinder of the actuator through a port in the cylinder, wherein actuation of the actuator through the introduction of the fluid into the cylinder causes an outward movement of the piston and rotation of the occluding member in a direction that moves the tube-compressing elements away from the pathways.

9. The occluder of claim 8, wherein the occluder comprises a lever arm mounted on the back surface of the base and having a first end connected to the occluding member pivot shaft and a second end connected to the actuating shaft, the lever arm being rotationally movable about the axis of the pivot shaft between a first position when the piston is in a retracted position and a second position when the piston is in an extended position, the lever arm rotating the occluding member from the occluding to the non-occluding position when the lever arm is moved from the first to the second position.

10. The occluder of claim 9, further comprising:
a biasing member comprising a spring mounted on the back surface of the base exerting a biasing force on the lever arm, the biasing force urging the occluding member to rotate the tube-compressing elements toward the pathways.

11. An occluder for occluding at least two collapsible tube of a medical infusion device, the occluder comprising:
a base having a front surface defining two substantially parallel pathways along each of which a length of at least one of the collapsible tubes can be placed, and having an opposing back surface onto which an occluder actuator is mounted, wherein the base is configured for mounting onto the medical infusion device;
an occluding member located on the front surface of the base between the pathways and comprising a pivot shaft having a long axis that extends through the base from the back surface to the front surface, and that is rotationally movable about a pivot axis coincident with the long axis of the pivot shaft, the pivot shaft being approximately perpendicular to said back and front surface of the base, the occluding member comprising a pair of tube-compressing elements on opposing sides of the pivot shaft that are rotationally movable upon rotation of the occluding member, such that when the at least two collapsible tubes are installed on the pathways of the front surface of the base, the tube-compressing elements at least partially obstruct both pathways and substantially restrict or essentially completely inhibit fluid flow through the collapsible tubes when the occluding member is in an occluding position but that does not obstruct the pathways and substantially restrict fluid flow through the collapsible tubes when the occluding member is in a non-occluding position;
the occluder actuator comprising an actuating shaft mechanically coupled to the pivot shaft, the actuating shaft having a long axis and a direction of travel that is approximately perpendicular to the pivot shaft and is arranged to cause rotation of the pivot shaft about the long axis of the pivot shaft, the occluder actuator further comprising a piston in a cylinder, the piston connected to the actuating shaft and moveable in the cylinder under a fluidic pressure delivered through a port in the cylinder; and
a grip member forming part of or immobilized with respect to the occluding member, the grip member being manually movable between a first position and a second position, wherein movement of the grip member from the first position into the second position moves the occluding member from the occluding position into the non-occluding position,
wherein actuation of the actuator through an introduction of a fluid into the cylinder causes an outward movement of the piston and rotation of the occluding member in a direction that moves the tube-compressing element away from the pathway.

12. The occluder of claim 11, further comprising:
a biasing member on the base and exerting a biasing force on the occluding member, the biasing force urging the occluding member to move into or remain in the occluding position.

13. The occluder of claim 11, wherein the occluder comprises a lever arm mounted on the back surface of the base and having a first end connected to the occluding member pivot shaft and a second end connected to the actuating shaft, the lever arm being rotationally movable about the axis of the pivot shaft between a first position when the piston is in a retracted position and a second position when the piston is in an extended position, the lever arm rotating the occluding member from the occluding position to the non-occluding position when the lever arm is moved from the first to the second position.

14. The occluder of claim 11, further comprising an openable cover mounted on the front surface of the base and adapted and configured to position and secure the tubes within the pathways when the cover is mounted onto the front surface of the base and in a closed position.

15. The occluder of claim 11, wherein the tube-compressing elements can progressively obstruct the pathways as the tube-compressing elements are moved to a position adjacent to the pathways and are advanced in a direction at least a part of which is parallel to the pathways.

16. An occluder for occluding at least two collapsible tubes of a medical infusion device, the occluder comprising:
a base having a front surface defining two substantially parallel pathways along each of which a length of at least one of the collapsible tubes can be placed, and having an opposing back surface onto which an occluder actuator is mounted, wherein the base is configured for mounting onto the medical infusion device;

an occluding member located on the front surface of the base and comprising a pivot shaft having a long axis that extends through the base from the back surface to the front surface, and that is rotationally movable about a pivot axis coincident with the long axis of the pivot shaft, the pivot shaft being approximately perpendicular to said back and front surface of the base, the occluding member comprising a pair of tube-compressing elements that are rotationally movable upon rotation of the occluding member, such that when the at least two collapsible tubes are installed on the pathways of the front surface of the base, the tube-compressing elements at least partially obstruct both pathways to substantially restrict or essentially completely inhibit fluid flow through the collapsible tubes when the occluding member is in an occluding position but that does not obstruct the pathways to substantially restrict fluid flow through the collapsible tubes when the occluding member is in a non-occluding position;

the occluder actuator comprising a pneumatic actuator and having a fluidic inlet and a piston in a cylinder, the piston movable from a first position to a second position when the fluidic inlet is pressurized, the movable piston being mechanically interconnected with the pivot shaft of the occluding member such that extension of the movable piston into the second position causes the occluding member to move into the non-occluding position; and a grip member forming part of or immobilized with respect to the occluding member, the grip member being manually movable between a first position and a second position, wherein movement of the grip member from the first position into the second position moves the occluding member from the occluding position into the non-occluding position.

17. The occluder of claim 16, further comprising a lever arm having a first end connected to the occluding member pivot shaft and a second end connected to the piston, the lever arm being rotationally movable about the axis of the pivot shaft between a first position when the piston is in a retracted position and a second position when the piston is in an extended position, the lever arm moving the occluding member from the occluding position to the non-occluding position when the lever arm is moved from the first to the second position.

18. The occluder of claim 17, further comprising a biasing spring on the back surface of the base and biased to move the lever arm into the first position.

19. The occluder of claim 16, further comprising a biasing member on the base and exerting a biasing force on the occluding member, the biasing force urging the occluding member to move into or remain in the occluding position.

20. The occluder of claim 16, further comprising an openable cover mounted on the front surface of the base and adapted and configured to position and secure the tubes within the pathways when the cover is mounted onto the base and in a closed position.

21. The occluder of claim 16, wherein the tube-compressing elements can progressively obstruct the pathways as the tube-compressing element portions are moved to a position adjacent to the pathways and are advanced in a direction at least a part of which is parallel to the pathways.

22. An occluder for occluding at least two collapsible tubes of a medical infusion device, the occluder comprising:

a base having a front surface defining two substantially parallel pathways along each of which a length of at least one of the collapsible tubes can be placed, and having an opposing back surface onto which an occluder actuator is mounted, wherein the base is configured for mounting onto the medical infusion device;

an occluding member located on the front surface of the base and comprising a pivot shaft having a long axis that extends through the base from the back surface to the front surface, and that is rotationally movable about a pivot axis coincident with the long axis of the pivot shaft, the pivot shaft being approximately perpendicular to said back and front surface of the base, the occluding member comprising a pair of tube-compressing elements that are rotationally movable upon rotation of the occluding member pivot shaft, such that when the at least two collapsible tubes are installed on the pathways of the front surface of the base, the tube-compressing elements at least partially obstruct the pathways to substantially restrict or essentially completely inhibit fluid flow through the collapsible tubes when the occluding member is in an occluding position but that does not obstruct the pathways to substantially restrict fluid flow through the collapsible tubes when the occluding member is in a non-occluding position;

a lever arm mounted on the back surface of the base and having a first end connected to the occluding member pivot shaft, the lever arm being rotationally movable about the axis of the pivot shaft to move the occluding member from the occluding position to the non-occluding position, the lever arm moving the occluding member between the first position and the second position when the lever arm is moved from the first to the second position;

the occluder actuator comprising a pneumatic actuator and comprising a movable piston in a cylinder having a pneumatic port, the piston being connected to a second end of the lever arm and extendable upon pneumatic pressurization of the actuator from a first position to a second position, wherein extension of the piston into the second position causes the lever arm to move from the first position to the second position and the occluding member to move from the occluding position into the non-occluding position; and a grip member forming part of or immobilized with respect to the occluding member, the grip member being manually movable between a first position and a second position, wherein movement of the grip member from the first position into the second position moves the occluding member from the occluding position into the non-occluding position.

23. The occluder of claim 22, further comprising an openable cover mounted on the front surface of the base and adapted and configured to position and secure the tube within the pathway when the cover is mounted onto the base and in a closed position.

24. The occluder of claim 22, wherein rotational movement of the occluding member causes at least a portion of the occluding member to move in an arc that is approximately tangential to the pathways; wherein upon rotation of the occluding member toward the occluding position, the tube-compressing elements rotate toward the pathways; wherein upon rotation of the occluding member toward the non-occluding position, the tube-compressing elements rotate away from the pathways.

25. The occluder of claim 22, further comprising: a biasing spring on the back surface of the base and biased to move the lever arm into the first position.

\* \* \* \* \*